US00PP15413P2

(12) United States Plant Patent
Thomsen

(10) Patent No.: US PP15,413 P2
(45) Date of Patent: Dec. 7, 2004

(54) *EUPHORBIA MILII* PLANT NAMED 'EROS'

(50) Latin Name: *Euphoriba milii*
Varietal Denomination: Eros

(75) Inventor: Steen Thomsen, Hjortebjerg (DK)

(73) Assignee: Gartneriet Hjortebjerg I/S (DK)

( * ) Notice: Subject to any disclaimer, the term of this patent is extended or adjusted under 35 U.S.C. 154(b) by 0 days.

(21) Appl. No.: 10/799,689

(22) Filed: Mar. 15, 2004

(51) Int. Cl.[7] ..... A01H 5/00
(52) U.S. Cl. ..... Plt./302
(58) Field of Search ..... Plt./302

*Primary Examiner*—Bruce R. Campell
*Assistant Examiner*—W C Haas
(74) *Attorney, Agent, or Firm*—Foley & Lardner, LLP

(57) ABSTRACT

A new distinct cultivar of *Euphorbia milii* plant named 'Eros', characterized by its bright red floral bracts color from R.H.S. 42B to R.H.S. 45C; very dense and bushy plant form; moderately vigorous growth habit; high number of flowers per plant borne on short green peduncles, R.H.S. 144A.

2 Drawing Sheets

Latin name of the genus and species of the plant claimed: *Euphorbia milii* Desmoul.
Variety denomination: 'Eros'.

BACKGROUND OF THE INVENTION

The present Invention relates to a new and distinct cultivar of *Euphorbia milii* plant, botanically known as *Euphorbia milii* Desmoul, commonly known by the name Crown of Thorns, and hereinafter referred to by the name 'Eros'.

The new *Euphorbia milii* is a product of a planned breeding program conducted by the Inventor, Steen Thomsen, in Haarslev, Fyn, Denmark. The new *Euphorbia milii* originated from a cross made in 2001 by the Inventor with unnamed cultivars of *Euphorbia milii* Desmoul. The male and female parental cultivars are unnamed, unpatented seedlings of *Euphorbia milii* Desmoul. The Inventor selected the new *Euphorbia milii* cultivar as a single plant from the progeny of the above cross in 2001 on the basis of flower and compact, freely branching habit. Plants of the new *Euphorbia milii* are upright, compact and have a unique color and abundant, medium sized flowers.

Asexual reproduction of the new cultivar by terminal cuttings taken and propagated and trial production batches at Hjortebjerg Nurseries, Denmark, has shown that the unique features of this new *Euphorbia milii* are stable and reproduced true to type in many successive generations.

BRIEF SUMMARY OF THE INVENTION

The following traits have been repeatedly observed and are determined to be the unique characteristics of 'Eros'. These characteristics in combination distinguish 'Eros' as a new and distinct cultivar:

1. Bright red floral bract color from R.H.S. 42B, to R.H.S. 45C.
2. Very dense and bushy plant form.
3. Moderately vigorous growth habit.
4. High number of flowers per plant borne on short green peduncles, R.H.S. 144A.

Plants of the cultivar 'Eros' can be compared to plants of the cultivar *Euphorbia milii* 'Themis' (unpatented). In side-by-side comparisons conducted by the Inventor in Haarslev, Denmark, plants of the cultivar 'Eros' and the cultivar 'Themis' differ in the following characteristics:

1. Plants of the new *Euphorbia milii* have striking red color and staminate cyathia with red glands.
2. Plants of the new *Euphorbia milii* have larger dark green leaves than 'Themis'.
3. Plants of the new *Euphorbia milii* have shorter and stiffer peduncles than plants of the cultivar 'Themis'.
4. Plants of the new *Euphorbia milii* are more compact than the plants of the cultivar 'Themis'.
5. Plants of the new *Euphorbia milii* have more flowers per plant than the plants of the cultivar 'Themis'.

Plants of the cultivar 'Eros' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying color photographs illustrate the overall appearance and details of flower form, color and structures of the new cultivar, showing the colors as true as it is reasonably possible to obtain in colored reproductions of this type. Colors in the photographs may differ slightly from the color values cited in the detailed botanical description, which more accurately describe the actual colors of the new *Euphorbia milii.*

The first photograph shows a top view of a typical full flowering plant of 'Eros' as grown in an 11 cm pot.

The second photograph shows a close up of the floral cymes.

DETAILED BOTANICAL DESCRIPTION

In the following description, color references are made to The Royal Horticultural Society Colour Chart, $4^{th}$ edition, where general terms of ordinary dictionary significance are used. Plants were grown under greenhouse conditions. Plants used for this description were grown for about 17 weeks after cutting and produced in 11 cm pots. Other pot sizes can be used. The plants are intended for indoor use or as a bedding plant in temperate climates although it is a perennial garden plant in tropical and subtropical areas.

Botanical classification: *Euphorbia milii* Desmoul. cultivar 'Eros'. Euphorbiaceae, Spurge family.

Parentage:

*Female parent.*—Unnamed seedling plant of *Euphorbia milii.*

*Male parent.*—Unnamed seedling plant of *Euphorbia milii.*

Propagation:

*Type cutting.*—Terminal vegetative cuttings taken from plants kept in the vegetative stage by shading and high temperatures (25C).

*Time to initiate roots.*—About 10 to 14 days at 18 to 21 C in tunnels in a greenhouse.

*Root description.*—Fine, well branched.

Plant description:

*Form.*—Perennial plant with upright plant habit. *Euphorbia milii* 'Eros' flowers in cymes with cyathia subtended by colored bracts. Freely branching with about 6 lateral flowering branches forming at every node; dense and bushy. Stems are square to pentagonal with ridges, about 10 mm thick at base. By each node appears singular rather stiff thorns 7–8 mm. Young thorns are brown: 200C; while the older ones becomes stiffer and changes color to gray, 201B.

Crop time: After rooting, about 16–18 weeks are required to produce finished flowering plants in 11 cm pots.

Plant height (soil level to top of plant plane): About 15 cm. Width: 17 cm.

Vigor: Moderately vigorous growth rate.

Foliage description: Leaves alternate, single, obovate, entire.

*Size.*—Length: 7 cm. Width: About 30 mm.

*Apex.*—Acute.

*Base.*—Cuneate to almost decussate.

*Texture.*—Smooth, waxy, dull., glabrous.

*Color.*—Young foliage, upper and lower surfaces: 137A and 146C, yellow-green. Mature foliage, upper and lower surfaces: 139B and 139B respectively. Venation, 139A.

Flower description:

*Flower arrangement and shape.*—Floral arrangements composed of cymes. The flowers (cyathia) are starkly reduced so only a gland and the reproductive organs are present. Subtending the cyathia are two colored bracts. The flowers are further complicated by the unique feature of funnel shaped floral buds appearing at the base of the bracts in two or more layers.

*Natural flowering season.*—Continuous throughout the spring and summer in subtropical and tropical regions. In colder climates season can be extended by greenhouse production with high temperatures and supplementary irradiance.

*Flower longevity on the plant.*—Longevity of individual flowers is highly dependent on temperature and light conditions 5 to 9 weeks. Bracts turn green with age. Entire cymes drop after withering.

*Inflorescence size.*—Diameter: About 3–4 cm, height: 8 cm.

*Flowers.*—3 mm diameter, Bracts: overlapping at base, ovoid to inverted cordate, approximately 9 mm in length by 14 mm in width color from 42B, red to 45C red, young bracts: 156C, yellow-green.

*Glands.*—5, from N25A shiny orange to 43C red during development.

*Anthers.*—Appear after flowers mature; stamen and pollen color 15A, yellow-orange.

*Pistil and stigma.*—Appear before cyathia mature; color 1C, greenish-yellow.

*Peduncle.*—Strength: strong. Length: About 3–4 cm. Diameter: About 2 mm. Color: 144A, green.

*Pedicels.*—1–2 cm long, 1 mm thick strong color: 156A, yellow-green.

Weather tolerance: Plants of the new *Euphorbia milii* have exhibited good tolerance to draught, rain and wind, however flowering may cease during cold and dark periods (<15C).

Pest tolerance: Plants of the new *Euphorbia milii* have exhibited good tolerance to following fungi: Mildew, and Thivaliopis. Also, they appear to be less infected by Thrips (Franklinellea).

I claim:

1. A new and distinct cultivar of *Euphorbia milii* plant named 'Eros', as illustrated and described herein.

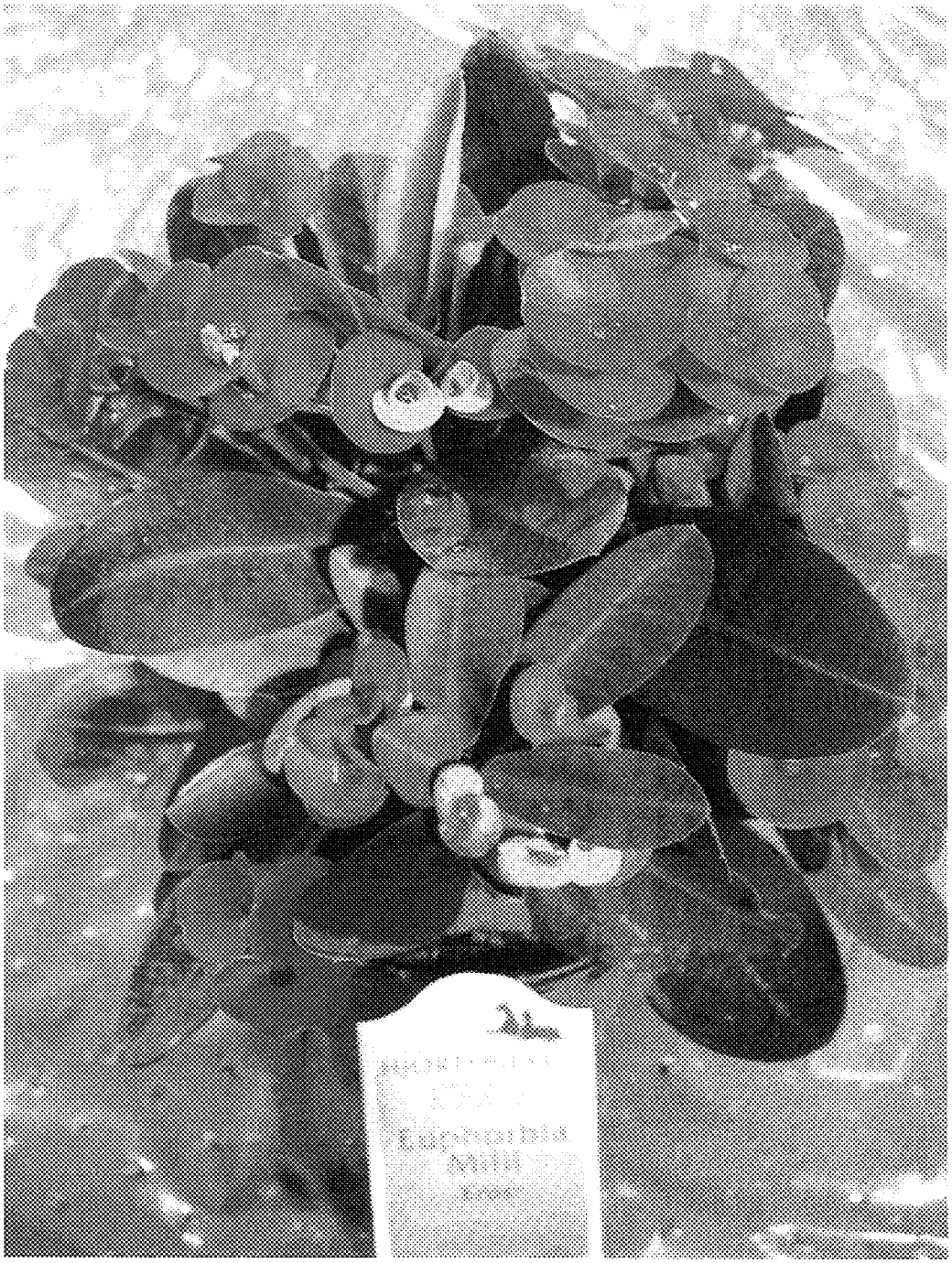

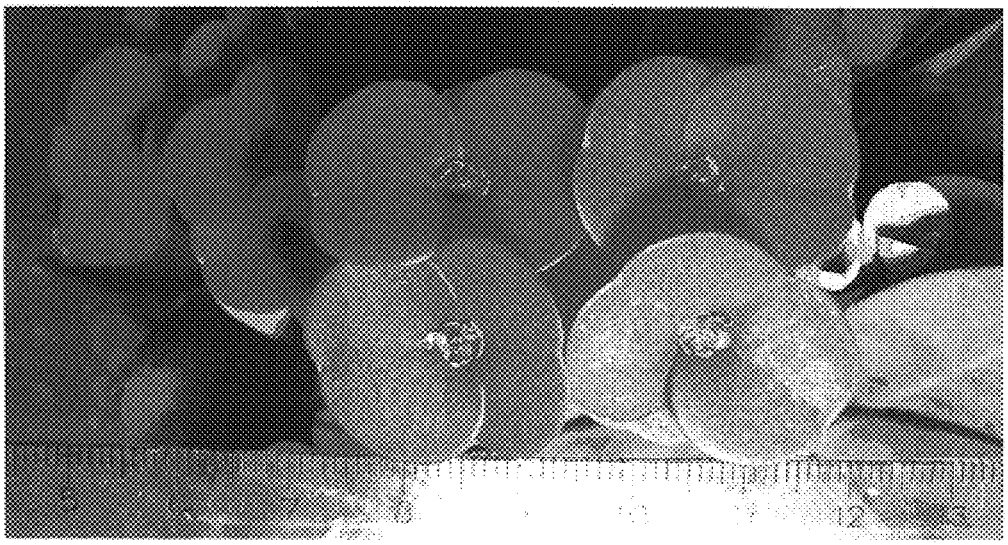

* * * * *